United States Patent [19]

Bender et al.

[11] Patent Number: 4,794,114
[45] Date of Patent: Dec. 27, 1988

[54] INHIBITION OF INTERLEUKIN-1 PRODUCTION BY MONOCYTES AND/OR MACROPHAGES

[75] Inventors: Paul E. Bender, Cherry Hill, N.J.; Don E. Griswold, North Wales, Pa.; Nabil Hanna, Berwyn, Pa.; John C. Lee, Radnor, Pa.

[73] Assignee: SmithKline Beckman Corporation, Philadelphia, Pa.

[21] Appl. No.: 63,550

[22] Filed: Jun. 17, 1987

Related U.S. Application Data

[63] Continuation-in-part of Ser. No. 897,909, Aug. 19, 1986, abandoned.

[51] Int. Cl.[4] .............................................. A61K 31/44
[52] U.S. Cl. .................................... 514/333; 514/885; 514/908
[58] Field of Search ................. 514/332, 333, 885, 908

[56] References Cited

U.S. PATENT DOCUMENTS

| 4,064,260 | 12/1977 | Chefkofsky et al. | 514/368 |
| 4,110,460 | 8/1978 | Baetz et al. | 514/368 |
| 4,153,706 | 5/1979 | Bender et al. | 514/368 |
| 4,175,127 | 11/1979 | Bender et al. | 514/333 |
| 4,186,205 | 1/1980 | Bender et al. | 514/393 |
| 4,263,311 | 4/1981 | Bender et al. | 514/368 |
| 4,507,481 | 3/1985 | Davidson et al. | 546/121 |

FOREIGN PATENT DOCUMENTS 2039882  8/1980  United Kingdom .

OTHER PUBLICATIONS

Lantos et al., *J. Med. Chem.*, 27, 72–75 (1984).
Bender et al., *J. Med. Chem.*, 28, 1169–1177 (1985).
Hagmann et al., *Naturwissenschaften*, 69, 594 (1982).
Galanos et al., *Proc. Natl. Acad. Sci.*, USA, 76, 5939 (1979).

*Primary Examiner*—John W. Rollins
*Attorney, Agent, or Firm*—Carol G. Canter; Edward T. Lentz; Alan D. Lourie

[57] ABSTRACT

A method of inhibiting the 5-lipoxygenase pathway in an animal in need thereof which comprises administering an effective, 5-lipoxygenase pathway inhibiting amount of a diaryl-substituted imidazole fused to a thiazole pyrrolidine, thiazide or piperidine ring to such animal.

20 Claims, No Drawings

INHIBITION OF INTERLEUKIN-1 PRODUCTION BY MONOCYTES AND/OR MACROPHAGES

CROSS REFERENCE TO RELATED APPLICATIONS

This application is a continuation-in-part of Ser. No. 897,909, filed Aug. 9, 1986 which is abandoned.

BACKGROUND OF THE INVENTION

This invention relates to a method of inhibiting the production of interleukin-1 by monocytes and/or macrophages in a human in need thereof which comprises administering to such human an effective, interleukin-1 production inhibiting amount of a diaryl-substituted imidazole fused to a thiazole, pyrrolidine or piperidine ring or a pharmaceutically acceptable salt thereof.

Ciba-Geigy AG., U.K. patent application GB 2,039,882, published Aug. 20, 1980, discloses compounds of the formula

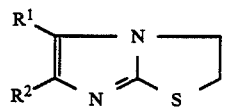

wherein the 1,3-diazacyclopent-2-ene ring may have a further double bond, Alk represents lower alkylene that separates the sulfur atom from the nitrogen atom by 2 to 4 carbon atoms, $Ar_1$ and $Ar_2$ represent, independently of one another, an optionally substituted phenyl, pyridyl or thienyl radical and n is 0, 1 or 2, provided that at least one of the radicals $Ar_1$ and $Ar_2$ is not phenyl when Alk represents ethylene and the 1,3-diazacyclopent-2-ene ring represents an imidazole ring, and the salts thereof. The Ciba-Geigy reference alleges that such compounds exhibit antiinflammatory and antiexudation effects in the rat kaolin paw-oedema test or in the rat turpentine pleuritis test; that the unsaturated compounds in particular exhibit an excellent effect in the adjuvant arthritis test; and that such compounds also have an analgesic effect as shown in the phenyl-p-benzoquinone test in mice; inhibit prostaglandin synthetase in vitro; protect against fatal pulmonary embolism in rabbits (i.e., are anti-thrombotic); and that the tetrahydro compounds exhibit a strong effect in the pertussis oedema test. The rat kaolin paw oedema test and the rat turpentine pleuritis test are useful in detecting compounds which are cyclooxygenase inhibitors but are of no known utility in detecting or suggesting compounds which are inhibitors of interleukin-1 (IL-1) production by monocytes and/or macrophages. The adjuvant arthritis test is useful for detecting compounds which are inhibitors of prostanoid synthesis, but is of no utility for disclosing or suggesting compounds which are inhibitors of IL-1 production by monocytes and/or macrophages. The phenyl-p-benzoquinone test is useful for detecting compounds which are cyclooxygenase inhibitors, but is of no known utility in detecting or suggesting compounds which are inhibitors of IL-1 production by monocytes and/or macrophages. The observation that compounds of the Ciba-Geigy reference inhibit prostaglandin synthetase in vitro (cyclooxygenase) is of no utility in detecting or suggesting compounds which are inhibitors of IL-1 product or by monocytes and/or macrophages. The observation that the compounds of the Ciba-Geigy reference are anti-thrombotic in rabbits is of no known utility in detecting or suggesting compounds which are inhibitors of IL-1 production by monocytes and/or macrophages. The pertussis oedema test is useful in detecting compounds which are cyclooxygenase inhibitors, but is of no known utility in detecting or suggesting compounds which are inhibitors of IL-1 production by monocytes and/or macrophages.

Bender et al., U.S. Pat. No. 4,175,127, issued Nov. 20, 1979 disclose compounds of the formula

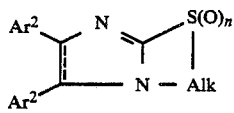

in which $R_1$ and $R_2$ are the same or different, but one of which always being pyridyl, are pyridyl or phenyl optionally monosubstituted by a lower alkoxy, lower alkyl, lower alkylthio, chloro, fluoro, bromo, or trifluoromethyl or a pharmaceutically acceptable acid addition salt or oxide derivative thereof. Bender et al. also discloses that such compounds have utility as antiarthritic agents. Such antiarthritic activity is disclosed as the result of test results from adjuvant-induced polyarthritis in rats. Although not claimed, the Bender patent also suggests, at column 3, lines 66–68, that compounds of Formula A also have inflammatory or immunoregulatory properties in addition to their antiarthritic activity. The Bender patent states, at column 4, lines 47–50, that such anti-inflammatory activity is produced by some of the Formula A compounds in the carrageenan-induced rat paw edema test which is useful for detecting compounds which are inhibitors of the cyclooxygenase pathway, but is of no known utility for detecting or suggesting compounds which are inhibitors of IL-1 production of monocytes and/or macrophages. The Bender patent also states, at column 4, lines 51–65, that species of the Formula A compounds have the ability to regulate cell-mediated immunity as shown in procedures such as the oxazolone-induced contact sensitivity test procedure in which mouse paw volume is measured. The oxazolone-induced contact sensitivity test is useful for detecting compounds which have immunostimulatory activity like levamisole but is of no known utility for detecting or suggesting compounds which are inhibitors of IL-1 production by monocytes and/or macrophages.

Lantos et al., *J. Med. Chem.*, 27, 72–75 (1984), also disclose that certain 5,6-diaryl-2,3-dihydroimidazo[2,1-b]thiazoles have antiinflammatory activity in the carrageenan-induced rat paw edema and adjuvant arthritis assay in rats. Both the adjuvant-induced polyarthritis assay in rats and the carrageenan-induced rat paw edema test are useful in detecting compounds which are inhibitors or prostanoid synthesis, mediated by the prostanoids formed by the enzyme cyclooxygenase, but are of no known utility in detecting or suggesting compounds which are inhibitors of IL-1 production by monocytes and/or macrophages. The oxazolone-induced contact sensitivity test in which mouse paw volume is measured is useful in detecting compounds which have immunostimulatory activity like levamisole, but is of no known utility in detecting or suggesting compounds which are inhibitors of IL-1 production by monocytes and/or macrophages.

Lantos et al., U.S. Ser. No. 737,137, filed May 29, 1985, disclose an improved method for the preparation of compounds of the formula:

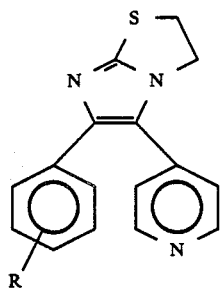

in which R is H, halo, $C_{1-2}$-alkyl, $C_{1-2}$-alkoxy or trifluoromethyl. Lantos et al. state that such compounds have antiarthritic activity. There is no further statement in this reference as to how such antiarthritic activity was determined. Such a blanket statement of antiarthritic utility does not disclose to one of skill in the art that such compounds are inhibitors of IL-1 production by monocytes and/or macrophages.

Cherkofsky et al., U.S. Pat. No. 4,064,260, issued Dec. 20, 1977 discloses compounds of the formula

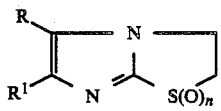

in which n is 0, 1 or 2, and R and $R^1$ are independently selected from monosubstituted phenyl wherein said substituent is selected from monosubstituted phenyl wherein said substituent is selected from $C_{1-4}$ alkoxy. Cherkofsky et al. also disclose that such compounds have utility as antiinflammatory agents as demonstrated by their activity in the established adjuvant-induced arthritis assay in rats or the phenylquinone writhing test in mice. As stated above, the adjuvant arthritis test is of no utility for disclosing or suggesting compounds which are inhibitors of IL-1 production by monocytes and/or macrophages.

Bender et al., U.S. Pat. No. 4,263,311 issued Apr. 21, 1981, discloses compounds of the formula

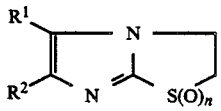

wherein n is 0, 1 or 2, and $R^1$ and $R^2$ are independently selected from (a) monosubstituted phenyl wherein said substituent is selected from lower alkoxy, chloro, fluoro, bromo, trifluoromethyl, amino, di-N-N-lower alkylamino or (b) 3,4-methylenedioxyphenyl. Bender et al. also disclose that such compounds have utility (a) in the treatment of arthritis based on their activity in the adjuvant-induced arthritis test in rats and in the carrageenan-induced rat paw edema test; and (b) as immunoregulatory agents based on their activity in the oxazolone-induced contact sensitivity test in which mouse paw volume is measured. As stated above, none of the adjuvant arthritis test, carrageenan edema test or oxazolone sensitivity test have any known utility in detecting or suggesting compounds which are inhibitors of IL-1 production by monocytes and/or macrophages.

Bender et al., U.S. Pat. No. 4,186,205, issued Jan. 29, 1980, disclose compounds of the formula

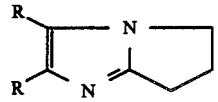

wherein R is 4-monosubstituted phenyl and said substituent is selected from $C_{1-4}$ alkoxy or chloro, or a nontoxic, pharmaceutically acceptable salt thereof. Bender et al. also disclose that such compounds are useful as (a) antiarthritic agents based on their activity in the adjuvant-induced arthritis assay in rats; and (b) regulators of cell-mediated immunity based on their activity in the oxazolone-induced contact sensitivity test in which mouse paw volume is measured. As stated above, neither the adjuvant arthritis test nor the oxazolone sensitivity test are of any known utility in disclosing or suggesting compounds which are inhibitors of IL-1 production by monocytes and/or macrophages.

Bender et al., *J. Med. Chem.*, 28, 1169–1177 (1985), disclose compounds of the formula

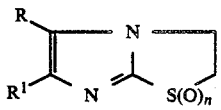

wherein n is 0, 1 or 2, and R and $R^1$ are independently selected from (a) monosubstituted phenyl wherein said substituent is selected from $C_{1-4}$ alkoxy, halo, 4-amino, 4-acetamido, 4-trifluoromethyl, 4-N(ethyl)-acetamido, 4-ethylamino, and 4-ethyl(methyl)amino; or (b) 3,4-methylenedioxyphenyl. Bender et al. also disclose that some of such compounds are useful as immunoregulatory, antiinflammatory and antiarthritic agents based on their activity in the adjuvant-induced arthritis test and the mouse subliminal oxazolone-induced contact sensitivity assay. As stated above, the adjuvant arthritis assay is of no utility in detecting or suggesting compounds which are inhibitors of IL-1 production by monocytes and/or macrophages. The mouse subliminal oxazolone sensitivity assay is useful in detecting compounds which are immunostimulatory but is of no known utility in detecting compounds which are inhibitors of IL-1 production by monocytes and/or macrophages.

Baetz et al., U.S. Pat. No. 4,110,460, issued Aug. 29, 1978, disclose compounds of the formula

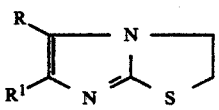

wherein R and $R^1$ are independently selected from monosubstituted phenyl wherein said substituent is selected from chloro, bromo, $C_{1-4}$ alkoxy, or a pharmaceutically acceptable acid addition salt thereof. Baetz et al. also disclose that such compounds have anti-inflammatory activity based on their activity in the carrageenan-induced edema assay in rats, cotton-induced granuloma assay in rats, ultraviolet induced erythema assay in guinea pigs, and Freund's-adjuvant induced arthritis assay in rats. All of such assays are useful for detecting compounds which are inhibitors of prostanoid synthesis, but none of such assays is of any known utility for disclosing or suggesting compounds which are inhibitors of IL-1 production by monocytes and/or macrophages. Baetz et al. also disclose that such compounds have utility as antipyretic agents based on their activity in an assay in which hyperthermia was induced in rats by subcutaneous injection with yeast. Such assay is useful for detecting compounds which are cyclooxygenase inhibitors but is of no known utility in detecting or suggesting compounds which are inhibitors of IL-1 production by monocytes and/or macrophages. Baetz et al. also disclose that such compounds have analgesic activity based on their activity in the acetic acid writhing test in mice. The acetic acid writhing test is useful for detecting compounds which are cyclooxygenase inhibitors but is of no known utility in detecting compounds which are inhibitors of IL-1 production by monocytes and/or macrophages.

Bender et al., U.S. Pat. No. 4,153,706, issued May 8, 1979, disclose compounds of the formula

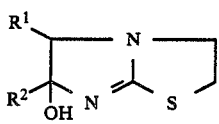

wherein $R^1$ is 4-substituted phenyl wherein said substituent is selected from lower alkoxy, lower alkylthio, fluoro, chloro, bromo or trifluoromethyl; and $R^2$ is 4-substituted phenyl wherein said substituent is an election withdrawing group, in particular, fluoro, chloro, bromo or trifluoromethyl. Bender et al. also state that such compounds have antiarthritic activity as measured in the adjuvant-induced polyarthritis assay in rats; and immunoregulatory activity as measured by the oxazolone-induced contact sensitivity test in mice. As stated above, such assays do not disclose or suggest that such compounds are inhibitors of IL-1 production by monocytes and/or macrophages.

Davidson et al., U.S. Pat. No. 4,507,481, issued Mar. 26, 1985, disclose compounds of the formula

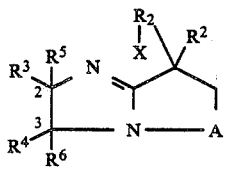

wherein
X is O or S(O)n;
n is 0, 1 or 2;
$R_1$ can be H;
$R_2$ can be H;
A is $CH_2$ or $CH_2CH_3$;
$R_3$ and $R_4$ are independently selected from phenyl substituted with lower alkyl, lower alkylamino, lower alkoxy or halogen;
$R_5$ and $R_6$ are each H or join to form a double bond at the 2,3-position.

Davidson et al. also disclose that such compounds are immunostimulants or immunosuppressants based on (a) their inhibiting or stimulating activity in a chemotaxis assay which measures the ability of a drug substance to influence the movement of murine macrophages responding to complement; (b) their immunosuppressing or activating activity in the Kennedy plaque assay in which an animal's humoral immune system is depressed artificially with 6-mercaptopyrine. Such chemotaxis assay is of no known utility for detecting or suggesting compounds which are inhibitors of IL-1 production by monocytes and/or macrophages. Davidson et al. also disclose that such compounds have antiinflammatory activity as determined by the carrageenan-induced paw edema assay in rats. As stated above, such assay has no known utility in detecting or suggesting compounds which are inhibitors of IL-1 production by monocytes and/or macrophages. Davidson et al. also disclose that such compounds have antiviral activity in mice with hepatitis; but such activity is of no known utility in detecting or suggesting compounds which are inhibitors of IL-1 production by monocytes and/or macrophages.

Hagmann et al., *Naturwissenschaften*, 69, 594 (1982), demonstrated that certain leukotriene antagonists and a Ca-calmodulin-specific inhibitor, calmidazolium, prevented endotoxin lethality in the murine model of endotoxin shock discussed in Galanos et al., *Proc. Natl. Acad. Sci. USA*, 76, 5939 (1979).

SUMMARY OF THE INVENTION

This invention relates to a method of inhibiting the production of interleukin-1 (IL-1) by monocytes and/or macrophages in a human in need thereof which comprises administering to such human an effective, IL-1 production inhibiting amount of a compound of the formula

Formula (I)

wherein:
One of $R^1$ and $R^2$ must be 4-pyridyl and the other is selected from 4-pyridyl or monosubstituted phenyl wherein said substituent is selected from halo or $C_{1-4}$ alkoxy;
X is $CH_2$, $CH_2CH_2$ or $S(O)n$; and
n is 0, 1 or 2;
or a pharmaceutically acceptable salt thereof.

DETAILED DESCRIPTION OF THE INVENTION

The preparation of all compounds of Formula (I) and pharmaceutically acceptable salts thereof is disclosed in Bender et al., U.S. patent application Ser. No. 856,875 filed Apr. 28, 1986 and Bender et al., U.S. patent application Ser. No. 856,928, filed Apr. 28, 1986, the disclosures of both of which are hereby incorporated by reference.

By the term "inhibiting the production of IL-1" is meant the down regulation of excessive in vivo IL-1 levels in a human to normal levels.

By the term "production of IL-1 by monocytes and/or macrophages" is meant the in vivo release of IL-1 by such cells.

Interleukin-1 (IL-1) has been recently demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels. However, much remains to be learned about the synthesis, processing and secretion of IL-1. For example, there is recent evidence suggesting that there are two separate human interleukin-1 genes, and that the products of these two genes differ in their isoelectric points. It is also clear that the published data on the cloning of the cDNA of the IL-1 gene(s) suggest that IL-1 is synthesized as a 31 kilodalton (Kd) precursor, which is subsequently processed to yield a smaller mature protein of about 17 Kd, the activity of which is detectable in culture supernatants. One interesting feature of the precursor protein is that it lacks a classical signal peptide sequence, suggesting that the molecule is probably not secreted in a classical manner. There is very little information available as to how the 31 Kd precursor is processed and secreted.

The discovery of a compound which specifically inhibits IL-1 production will not only contribute to the understanding of how this molecule is synthesized, processed and secreted, but will also provide a therapeutic approach for diseases in which excessive or unregulated IL-1 production is implicated.

It has now been discovered that compounds of Formula (I) and pharmaceutically acceptable salts thereof are useful for inhibiting the production of IL-1 by monocytes and/or macrophages in a human in need of such inhibition.

There are several disease states in which excessive or unregulated IL-1 production by monocytes and/or macrophages is implicated in exacerbating and/or causing the disease. These include rheumatoid arthritis [See, e.g., Fontana et al., *Arthritis Rheum.*, 22, 49–53 (1982)]; osteoarthritis [See, e.g., Wood et al., *Arthritis Rheum.*, 26, 975 (1983)]; toxic shock syndrome [See, e.g., Ikejima and Dinarello, *J. Leukocyte Biology*, 37, 714 (1985)]; other acute or chronic inflammatory disease states such as the inflammatory reaction induced by endotoxin [See, e.g., Habicht and Beck, *J. Leukocyte Biology*, 37, 709 (1985)]; and other chronic inflammatory disease states such as tuberculosis. [See, e.g., Chesque et al., *J. Leukocyte Biology*, 37, 690 (1985)]. Benjamin et al., "Annual Reports in Medicinal Chemistry—20", Chapter 18, pages 173–183 (1985), Academic Press, Inc., disclose that excessive IL-1 production is implicated in: Psoriatic arthritis, Reiter's syndrome, Rheumatoid arthritis, Osteoarthritis, Gout, Traumatic arthritis, Rubella arthritis, and Acute synovitis.

Dinarello, *J. Clinical Immunology*, 5 (5), 287–297 (1985), reviews the biological activities which have been attributed to IL-1 and such activities are summarized in Table A.

Table A

Biological Activities Attributed to IL-1

Fever (in rabbits, mice and rats)
Hypoferremia
Hypozincemia
Hypercupremia
Increased
   Blood neutrophils
   Hepatic acute-phase proteins
   Bone resorption
   Cartilage breakdown
   Muscle proteolysis
   Slow-wave sleep
   Endothelial procoagulant
   Chondrocyte proteases
   Synovial collagenase
   Endothelial neutrophil adherence
   Neutrophil degranulation
   Neutrophil superoxide
   Interferon production
Proliferation of
   Fibroblasts
   Glial cells
   Mesangial cells
   Synovial fibroblasts
   EBV B-cell lines
Chemotaxis of
   Monocytes
   Neutrophils
   Lymphocytes
Stimulation of $PGE_2$ in
   Hypothalamus
   Cortex
   Skeletal muscle
   Dermal fibroblast
   Chondrocyte
   Macrophage/monocyte
   Endothelium ($PGI_2$)
Decreased
   Hepatic albumin synthesis
   Appetite
   Brain binding of opioids
Augmentation of
   T-cell responses
   B-cell responses
   NK activity
   IL-2 production
   Lymphokine production An effective, IL-1 production inhibiting amount of a compound of Formula (I) or a pharmaceutically acceptable salt thereof is useful in treating, prophylactically or therapeutically, any disease state in a human which is exacerbated or caused by excessive or unregulated IL-1 production by such human's monocytes and/or macrophages. Preferably, the disease state is endotoxin-induced shock.

This invention relates to a method of inhibiting the production of IL-1 by monocytes and/or macrophages in a human in need thereof which comprises administering an effective, IL-1 production inhibiting amount of a compound of Formula (I) or a pharmaceutically acceptable salt thereof to such human. A compound of Formula (I) or a pharmaceutically acceptable salt thereof can be administered to such human in a conventional dosage form prepared by combining a compound of Formula (I), or a pharmaceutically acceptable salt thereof, with a conventional pharmaceutically acceptable carrier or diluent according to known techniques, such as those described in Bender et al., U.S.S.N. 856,875 filed Apr. 28, 1986 and Bender et al., U.S.S.N. 856,928, filed Apr. 28, 1986. It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt thereof is administered to a human in need of inhibition of IL-1 production by its monocytes and/or macrophages in an amount sufficient to inhibit such excessive IL-1 production to the extent that it is regulated down to normal levels. The route of administration may be oral, parenteral or topical. The term parenteral as used herein includes intravenous, intramuscular, subcutaneous intranasal, intrarectal, intravaginal or intraperitoneal administration. The subcutaneous and intramuscular forms of parenteral administration are generally preferred. The daily oral dosage regimen will preferably be from about 5 to about 100 mg/kilogram of total body weight. The daily parenteral dosage regimen will preferably be from about 2 to about 80 mg per kilogram (kg) of total body weight, most preferably from about 3 to about 60 mg/kg. The daily topical dosage regimen will preferably be from about 2 mg to about 10 mg per site of administration. It will be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way.

As used herein, the term "Compound 1" refers to the compound of Formula (I) wherein $R^1$ is 4-pyridyl, $R^2$ is 4-fluorophenyl, X is S(O)n and n is 0, and the term "Compound 5" refers to the compound of Formula (I) wherein $R^1$ is 4-pyridyl, $R^2$ is 4-flurophenyl and X is $CH_2$.

EXAMPLE 1

Inhibitory Effect of a Compound of Formula (I) on in vitro IL-Production by Human Monocytes The effects of antiinflammatory/antiarthritic drugs of different classes, including Compound 1 on the in vitro production of IL-1 by human monocytes was examined.

Bacterial lipopolysaccharide (LPS) was used to induce IL-1 production by human peripheral blood monocytes. IL-1 activity was measured by its ability to stimulate a Interleukin 2 (IL-2) producing cell line (EL-4) to secrete IL-2, in concert with A23187 ionophore, according to the method of Simon et al., J. Immunol. Methods, 84, 85, (1985). Human peripheral blood monocytes were isolated and purified from either fresh blood preparations from volunteer donors, or from blood Bank buffy coats, according to the procedure of Colotta et al., J. Immunol., 132, 936 (1984). $1 \times 10^6$ of such monocytes are plated in 24-well plates at a concentration of 2 million/ml per well. The cells were allowed to adhere for 2 hours, after which time nonadherent cells were removed by gentle washing. Test compounds were then added to the cells for 1 hour (hr) before the addition of lipopolysaccharide (10 ng/ml unless otherwise noted), and the cultures were incubated at 37° C. for an additional 24 hours. At the end of the incubation period, culture supernatants were removed and clarified of cells and all debris. Culture supernatants were immediately assayed for IL-1 biological activity as well as prostaglandin and/or leukotriene concentrations by radioimmunoassay.

The results indicated that human peripheral blood monocytes are exquisitely sensitive to bacterial endotoxin. Nanogram or even picogram quantities of LPS stimulated high levels of IL-1 production as well as prostaglandin production; however, little, if any, leukotriene was detected in such supernatants. These observations are consistent with previous reports [(See, Humes et al., J. Biol. Chem., 257, 1591 (1982)]. As shown in Table 1, ibuprofen, although highly active in inhibiting prostaglandin synthesis, had virtually no effect on IL-1 production. The 5-lipoxygenase (5-LO) inhibitors phenidone and nordihydroguaiaretic acid (NDGA) were marginally active in inhibition of IL-1 production and, interestingly, had little inhibitory effect on prostaglandin synthesis. Compound 1, however, was active in submicromolar range ($10^{-7}$M), resulting in greater than 80% inhibition of both prostaglandin synthesis and IL-1 production. Chloroquine, an antiarthritic/antimalarial compound previously demonstrated to inhibit IL-1 production, [See, Lipsky, Amer. J. Med. 75, Supp. 1A, 19 (1983)] was only marginally active at doses one or two logs higher than that of Compound 1.

Inhibition of IL-1 production by Compound 1 is not due to a carryover effect of the drug on the cells sed in the IL-1 readout assay. Various doses of Compound 1 were tested for its activity effects on a preparation of Il$^{-1}$ standard on the EL-4/CTLL assay. At high concentrations (i.e., $10^{-5}$ or higher), compound 1 had an effect on the assay system, perhaps a result of toxic effects on the cells; however, at lower doses of Compound 1 there was no direct effect on the IL-1 assay per se. It has been further demonstrated that Compound 1 does not exert a nonspecific toxic effect on other functions of activated monocytes. LPS-treated human monocytes can mediate a potent tumoricidal activity in the kill of A375 melanoma cells, as previously demonstrated [See, Kleinerman et al., J. Clin. Inves., 72, 304 (1983)]. Compound 1, at concentrations ranging from $10^{-5}$ to $10^{-8}$M did not effect that biological activity. Furthermore, the possibility that Compound 1 treatment of monocytes in presence or absence of LPS may have induced an inhibitor which interfered with the IL-1 assay was also ruled out (data not shown).

The in vitro inhibition of IL-1 production by Compound 1 is dose dependent. There is little, if any, difference between the effect of the drug at any given concentration of LPS. This observation, along with the fact that there was always a residual IL-1 activity remaining over a wide range of LPS used, suggests that the inhibitory effect of Compound 1 on IL-1 production remains constant, i.e., about 80% inhibition of $10^{-6}$M and about 40% inhibition at $10^{-7}$M.

The exact mechanism by which Compound 1 inhibits in vitro IL-1 production by monocytes is not presently known. It is clear, however, that while Compound 1 inhibits IL-1 production induced by a variety of activators, its inhibition is IL-1 specific, i.e., other inducible proteins such as alpha interferon are not effected. It is also clear that Compound 1 is not immunosuppressive and does not inhibit lectin-stimulated mitogenesis of human peripheral blood lymphocytes. Furthermore, it does not inhibit either IL-2 production or response.

The data in Table 1 shows that Compound 1 inhibits IL-1 production by human monocytes in vitro. This inhibitory activity does not seem to correlate with the property of the compound in mediating arachidonic acid metabolism inhibition since other nonsteroidal anti-inflammatory drugs with potent cyclooxygenase and-/or lipoxygenase inhibitory activity do not inhibit IL-1 production at nontoxic doses. Furthermore, inhibition of prostaglandin and/or leukotriene synthesis by a compound does not correlate with its ability to inhibit IL-1 production.

TABLE 1

| Compound[a] | M | % Inhibition PGE$_2$[c] | IL-1 |
|---|---|---|---|
| Ibuprofen | $10^{-5}$ | 97 | 9 |
| | $10^{-6}$ | 71 | 0 |
| | $10^{-7}$ | 63 | 0 |
| Phenidone | $10^{-7}$ | 63 | 0 |
| | $10^{-6}$ | 0 | 18 |
| | $10^{-7}$ | 0 | 0 |
| NDGA | $10^{-5}$[b] | 25 | 88 |
| | $10^{-6}$ | 0 | 33 |
| | $10^{-7}$ | 0 | 31 |
| Compound 1 | $10^{-5}$ | 99 | 99 |
| | $10^{-6}$ | 94 | 96 |
| | $10^{-7}$ | 79 | 88 |
| Chloroquine | $10^{-5}$ | 84 | 89 |
| | $10^{-6}$ | 0 | 46 |
| | $10^{-7}$ | 0 | 36 |

[a]All compounds, except chloroquine, were dissolved in absolute ethanol at $10^{-2}$ M, which was subsequently diluted further in tissue culture media. Ethanol control at dilution indicated that it did not affect the IL-1 assay. None of the compounds had a direct effect on the assay system at doses tested. Furthermore, test samples were dialyzed prior to testing in the IL-1 assay.
[b]At doses at or above $10^{-5}$ M, this compound exerted some toxic effects on monocytes, i.e., viability ~50% after 24 hours.
[c]PGE$_2$ was assayed using an RIA kit.

EXAMPLE 2

Inhibitory Effect of Major Metabolites of Compound 1 on In Vitro Production of IL-1 by Human Monocytes In order to elucidate the mechanism by which Compound 1 mediates its anti-inflammatory activity, the ability of this compound and two closely related analog metabolites, (i.e., the analogs of Compound 1 wherein X is S(O)n and n is 1 or 2) to inhibit human IL-1 production in vitro was evaluated according to the method of Example 1. Briefly, $1 \times 10^6$ human peripheral blood monocytes were plated in 24-well plates and allowed to adhere for 1 hr at 37° C. The above compounds were added to a final concentration of $10^{-5}$M to $10^{-8}$M. The monocytes were stimulated to produce IL-1 with 1 ng/ml LPS after a 1 hr pretreatment of the cells with the respective compounds. Table 2 summarizes the results obtained and shows that all three compounds of Formula (I) dramatically inhibit IL-1 production. Compound 1 appears to be slightly more potent than the two analogs tested.

TABLE 2

Formula (I)

| Compound No. | $R^1$ | $R^2$ | X | n | IC$_{50}$ ($\mu$M) |
|---|---|---|---|---|---|
| 1 | 4-pyridyl | 4-fluorophenyl | S(O)n | 0 | 0.25 |
| 2 | 4-pyridyl | 4-fluorophenyl | S(O)n | 1 | 0.80 |

TABLE 2-continued

Formula (I)

| Compound No. | $R^1$ | $R^2$ | X | n | IC$_{50}$ ($\mu$M) |
|---|---|---|---|---|---|
| 3 | 4-pyridyl | 4-fluorophenyl | S(O)n | 2 | 0.61 |

EXAMPLE 3

Effect of Compounds of Formula (I) on IL-1 Production by Human Monocytes

The inhibitory effect of additional compounds of Formula (I) on the in vitro production of IL-1 production of IL-1 by human monocytes was determined according to the procedure of Examples 1 and 2. Table 3 summarizes the results obtained. As indicated by Table 3, all compounds of Formula (I) inhibit IL-1 production.

TABLE 3

Formula I

| Compound No. | $R_1$ | $R_2$ | X | n | % Inhibition @ $10^{-6}$ M |
|---|---|---|---|---|---|
| 1 | 4-pyridyl | F$\phi$[a] | S(O)n | 0 | 70 |
| 2 | 4-pyridyl | F$\phi$ | S(O)n | 1 | 56 |
| 3 | 4-pyridyl | F$\phi$ | S(O)n | 2 | 54 |
| 4 | F$\phi$ | 4-pyridyl | S(O)n | 0 | 46 |
| 5 | 4-pyridyl | F$\phi$ | CH$_2$ | — | 78 |
| 6 | 4-pyridyl | MeO$\phi$[b] | S(O)n | 0 | 64 |
| 7 | 4-pyridyl | MeO$\phi$ | CH$_2$ | — | 40 |
| 8 | 4-pyridyl | MeO$\phi$ | CH$_2$CH$_2$ | — | 30 |

[a]F$\phi$ = 4-fluorophenyl
[b]MeO$\phi$ = 4-methoxyphenyl

EXAMPLE 4

Adjuvant-induced arthritis in the rat is a model of systemic inflammation with characteristics similar to rheumatoid arthritis in man. Arthritic rats exhibit many alterations associated with macrophage activation including increased production of IL-1 by LPS-stimulated splenic adherent macrophages in vitro. This model was employed to assess the effect of Compound 1 in vivo on this elevated IL-1 production. Briefly, rats were injected on day 0 with Freund's complete adjuvant in the right hind leg. Drugs were prepared as a suspension in tragacanth and administered daily per os either prophylactically (days 1 to 16) or therapeutically in a short-term modality (days 14 to 16). In all cases, final administration of drug occurred at 3 hours prior to sacrifice. Spleens were removed from these rats and the adherent cells were assessed for their ability to produce IL-1 in vitro in response to stimulation by LPS.

Tables 4a and 4b summarize the data from a typical experiment. In the case of prophylactic administration, Compound 1 produced a more dramatic decrease in IL-1 production than indomethacin which resulted in nearly complete normalization of this parameter. It is interesting to note that no effect was also observed in adjuvant arthritic rats therapeutically treated with Compound 1 or with a variety of clinically effective and commercially marketed human antiarthritic agents such as auranofin, methotrexate, d-penicillamine and indomethacin. Hence, the prescribed short-term treatment of an ongoing arthritic disease in the adjuvant-induced arthritic rat model does not adequately reflect therapeutic efficacy of known or potentially useful antiarthritic drugs.

Based on the widely held belief of the role of unmodulated (i.e., excessive) in vivo IL-1 production in causing or aggravating inflammatory responses and other disease states (see, e.g., Fontana et al., supra; Wood et al., supra; Akejima and Dinarello, supra; Habicht and Beck, supra; Chesque et al., supra; Benjamin et al., supra; and Dinarello, supra), and based on the fact that compounds of Formula (I) inhibit in vitro IL-1 production by human macrophages and/or monocytes (see, Tables 1, 2 and 3), as well as the fact that a compound of Formula (I) prophylactically inhibited such IL-1 production in the adjuvant-induced arthritic rat (see, Table 4a), and also the fact that compounds of Formula (I) prophylactically inhibited LPS-induced endotoxin shock in a murine model (Example 5, infra), it is expected that all compounds of Formula (I) inhibit the in vivo IL-1 production by monocytes and/or macrophages in a human in need thereof when used according to the method of the subject invention.

0.1 ug becomes a lethal dose (Table 5). The concentration of D-GALN required to obtain this effect is 400–500 mg/kg.

RESULTS

Dexamethasone provided protection when administered to the animals 24 hours and 1 hour prior to LPS/GALN administration.

Compound 1 also protected the animals from the lethal effects of LPS/GALN. Protection was obtained when Compound 1 was administerrd 1 hour prior to the injection of LPS/GALN and varied from 50 to 100% protection. Other compounds tested that have shown protective effects in this model are, Compound 5 phenidone (a dual inhibitor of arachidonic acid metabolism), and the histamine $H_1$ antagonist chlorpheniramine (but not the $H_2$ antagonist cimetidine).

TABLE A

Lethality of LPS in D-Galactosamine Treated C57B1/6 Mice

| Treatment | Lethality No. of Death/Total No. | |
|---|---|---|
| | 6 Hr. | 24 Hr. |
| LPS 100 ug | 0/10 | 0/10 |
| D-Galactosamine 500 mg/kg | 0/10 | 0/10 |
| D-Galactosamine 500 mg/kg | | |

TABLE 4A

| | AA | COMPOUND 1 | INDO-METHACIN | PREDNISOLONE | METHOTREXATE | D-PENI-CILLAMINE |
|---|---|---|---|---|---|---|
| | | | % NORMAL CONTROL | | | |
| | | | PROPHYLACTICS STUDIES | | | |
| RIGHT LEG PAW EDEMA | 197 ± 9 | 134 ± 9*** | 113 ± 8*** | 125 ± 22*** | 96 ± 4*** | 184 ± 20 |
| SPLENIC ADHERENT CELLS | | | | | | |
| % Adherent Cells | 357 ± 235 | 98 ± 29** | 480 ± 189 | 184 ± 79 | 134 ± 10* | 372 ± 117 |
| IL-1 Production | 368 ± 148 | 139 ± 28*** | 274 ± 100 | 168 ± 40** | 67 ± 56*** | 336 ± 170 |
| | | | THERAPEUTIC STUDIES | | | |
| RIGHT LEG PAW EDEMA | 193 ± 6 | 159 ± 7*** | 145 ± 18*** | 147 ± 18*** | 194 ± 2 | 191 ± 13 |
| SPLENIC ADHERENT CELLS | | | | | | |
| % Adherent Cells | 271 ± 118 | 216 ± 137 | 394 ± 253 | 82 ± 47 | 284 ± 175 | 217 ± 6 |
| IL-1 Production | 461 ± 201 | 392 ± 129 | 330 ± 121 | 300 ± 280 | 436 ± 178 | 374 ± 187[a] |

PROPHYLACTIC TREATMENT: Drugs were administered daily p.o. as a suspension in tragacanth from day 1 to day 16. Final dose given 3 hrs before sacrifice.
THERAPEUTIC TREATMENT: Drugs were administered daily p.o. as above from day 14 to day 16. Final dose given 3 hrs before sacrifice.
***$P < 0.01$ Indomethacin 2.0 mg/kg
**$P < 0.05$ Compound 1 60 mg/kg
*$P < 0.10$ Prednisolone 10 mg/kg
Methotrexate 0.3 mg/kg
D-Penicillamine 50 mg/kg
[a]$N = 2$

EXAMPLE 5

EFFECT OF COMPOUNDS OF FORMULA I IN ENDOTOXIN SHOCK

Model of endotoxin shock in C57B1/6 Mice

Mice are very resistant to the lethal effects of bacterial lipopolysaccharides (LPS). D-Galactosamine (D-GALN) induces a high degree of sensitization to the lethal effects of LPS in mice and other experimental animals. [See, Galanos et al., Proc. Natl. Acad Sci. USA., 76, 5939 (1979)]. In mice, depending on the strain and age, the sensitivity to endotoxin can be increased many thousand-fold.

A number of preliminary experiments were carried out to establish this model of lethal endotoxin shock. LPS concentrations of up to 1 mg/mouse are not lethal in C57B1/6 mice. When injected i.v. with D-GALN (500 mg/kg), however, the sensitivity increases so that

| +LPS | | |
|---|---|---|
| 1 ug | 8/10 | 10/10 |
| .1 ug | 9/10 | 10/10 |
| .01 ug | 1/10 | 5/10 |

All compounds were administered i.v.

D-Galactosamine sensitized mice to the lethal effect of 0.1 ug of LPS. Treatment with 0.01 ug of LPS resulted in 50% lethality 6–24 hours following the injection of LPS/D-GALN.

What is claimed is:
1. A method of inhibiting the production of interleukin-1 by monocytes and/or macrophages in a human in need thereof which comprises administering to such human an effective, interleukin-1 production inhibiting amount of a compound of the formula

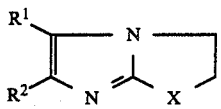

Formula (I)

wherein:
One of $R^1$ and $R^2$ must be 4-pyridyl and the other is selected from monohalosubstituted phenyl wherein said substituent is selected from halo or $C_{1-4}$ alkoxy;
X is $CH_2$, $CH_2CH_2$ or $S(0)n$; and
n is 0, 1 or 2;
or a pharmaceutically acceptable salt thereof.

2. The method of claim 1 wherein the route of administration is parenteral.

3. The method of claim 2 wherein the route of administration is intravenous or intramuscular.

4. The method of claim 2 wherein the compound is administered on a daily dosage regimen of from about 2 to about 80 mg per kg of total body weight.

5. The method of claim 4 wherein the daily dosage regimen is from about 3 to about 60 mg/kg of total body weight.

6. The method of claim 1 wherein the route of administration is oral.

7. The method of claim 6 where the compound is administered on a daily dosage regimen of from about 5 to about 100 mg/kg of total body weight.

8. The method of claim 1 wherein the route of administration is topical.

9. The method of claim 8 wherein the daily topical dosage regimen is from about 2 mg to about 10 mg per site of administration.

10. The method of claim 1 wherein $R^1$ is 4-pyridyl, $R^2$ is 4-fluorophenyl, X is S(0) and n is 0.

11. The method of claim 1 wherein $R^1$ is 4-pyridyl, $R^2$ is 4-fluorophenyl, X is S(0)n and n is 1.

12. The method of claim 1 wherein $R^1$ is 4-pyridyl, $R^2$ is 4-fluorophenyl, X is S(0)n and n is 2.

13. The method of claim 1 wherein $R^1$ is 4-fluorophenyl, $R^2$ is 4-pyridyl, X is S(0)n and n is 0.

14. The method of claim 1 wherein $R^1$ is 4-pyridyl, $R^2$ is 4-fluorophenyl and X is $CH_2$.

15. The method of claim 1 wherein $R^1$ is 4-pyridyl, $R^2$ is methoxyphenyl, X is S(0)n and n is 0.

16. The method of claim 1 wherein $R^1$ is 4-pyridyl, $R^2$ is 4-methoxyphenyl and X is $CH_2$.

17. The method of claim 1 wherein $R^1$ is 4-pyridyl, $R^2$ is 4-methoxyphenyl and X is $CH_2CH_2$.

18. The method of claim 1 wherein the human is afflicted with endotoxin-induced shock.

19. The method of claim 18 wherein $R^1$ is 4-pyridyl, $R^2$ is 4-fluorophenyl, X is S(0)n and n is 0.

20. The method of claim 18 wherein $R^1$ is pyridyl, $R^2$ is 4-fluorophenyl and X is $CH_2$.

* * * * *

UNITED STATES PATENT AND TRADEMARK OFFICE
CERTIFICATE OF CORRECTION

PATENT NO. : 4,794,114

DATED : December 27, 1988

INVENTOR(S) : Paul E. Bender et al.

It is certified that error appears in the above-identified patent and that said Letters Patent is hereby corrected as shown below:

In Claim 10, at column 16, line 10, delete "S(O)" and insert therefor -- $S(O)_n$ --

Signed and Sealed this

Sixth Day of June, 1989

*Attest:*

DONALD J. QUIGG

*Attesting Officer*  *Commissioner of Patents and Trademarks*